Figure 2:
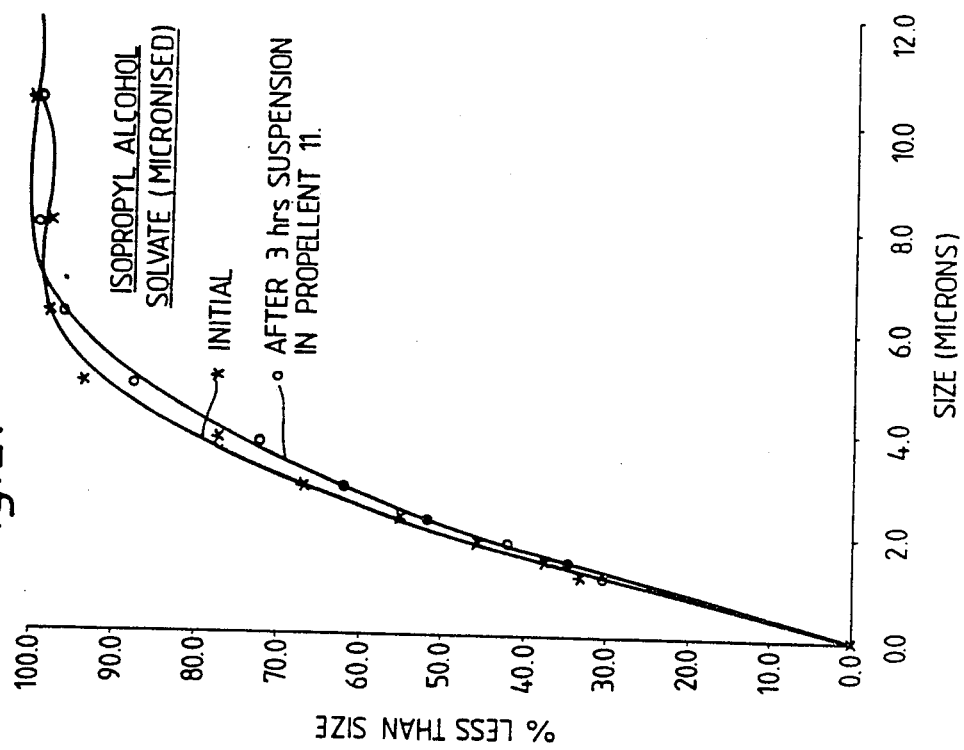

United States Patent [19]
Jinks

[11] Patent Number: 4,810,488
[45] Date of Patent: Mar. 7, 1989

[54] PHYSICALLY MODIFIED BECLOMETHASONE DIPROPIONATE SUITABLE FOR USE IN AEROSOLS

[75] Inventor: Philip A. Jinks, Mountsorrel, Great Britain

[73] Assignee: Riker Laboratories, Inc., St. Paul, Minn.

[21] Appl. No.: 902,411

[22] PCT Filed: Dec. 16, 1985

[86] PCT No.: PCT/GB85/00588

§ 371 Date: Aug. 18, 1986

§ 102(e) Date: Aug. 18, 1986

[87] PCT Pub. No.: WO86/03749

PCT Pub. Date: Jul. 3, 1986

[30] Foreign Application Priority Data

Dec. 19, 1984 [GB] United Kingdom ............... 8432063

[51] Int. Cl.$^4$ ............................. A61L 9/04; C07J 5/00
[52] U.S. Cl. ................................. 424/45; 260/397.45
[58] Field of Search ..................... 424/45; 260/397.45

[56] References Cited

FOREIGN PATENT DOCUMENTS 0039369 11/1981 European Pat. Off. .
3018550 12/1980 Fed. Rep. of Germany .
1429184 3/1976 United Kingdom .
2107715 5/1983 United Kingdom .

*Primary Examiner*—Mary C. Lee
*Assistant Examiner*—Bernard I. Dentz
*Attorney, Agent, or Firm*—Donald M. Sell; Walter N. Kirn; Robert W. Sprague

[57] ABSTRACT

A method for preparing a stable aerosol formulation of beclomethasone dipropionate in which the steroid is contacted with an alcohol containing 1 to 5 carbon atoms to form a crystalline solvate therewith, the crystalline material so formed being reduced to a particle size below 10 microns and thereafter dispersed in a composition comprising chlorofluorocarbon propellents.

10 Claims, 1 Drawing Sheet

PHYSICALLY MODIFIED BECLOMETHASONE DIPROPIONATE SUITABLE FOR USE IN AEROSOLS

This invention relates to beclomethasone dipropionate and in particular to the physical modification thereof to provide crystals suitable for incorporation into stable suspension aerosol formulations.

Anti-inflammatory steroids, e.g. beclomethasone dipropionate, have been micronised into particles of a size suitable for endopulmonary or nasal inhalation, i.e. particles in the size range 2 to 5 microns, which display crystal growth when incorporated into aerosol formulations containing halogenated hydrocarbons, e.g. trichloromonofluoromethane (Propellant 11), dichlorotetrafluoroethane (Propellent 114) and dichlorodifluoromethane (Propellent 12). Crystals of a size larger than 20 microns are formed and such crystals are unsuitable for inhalation since their particle size is too great adequately to penetrate the trachea or nasal cavities. Investigations have revealed that the large crystals are not pure steroid but a solvate with one of the propellents, particularly Propellent 11.

There are several methods of inhibiting or reducing crystal growth of steroids in chlorofluorocarbon propellents.

British Patent Specification No. 1 429 184 discloses the preparation of a stable aerosol formulation in which the steroid is contacted with a halogenated hydrocarbon to form a crystalline solvate therewith, the crystalline solvate so formed being reduced to a particle size suitable for inhalation and thereafter being dispersed in an aerosol propellent.

United Kingdom Patent Application No. GB 2076422A discloses a process in which the increase of particle size is prevented at the suspending stage when the solubility of the steroid is reduced by using a low temperature (5° to −40° C.) and by initially mixing only a small quantity of the propellent with the steroid.

German Offenlegungsschrift No. 3 018 550 discloses the formation of a solvate of beclomethasone dipropionate with ethyl acetate, reducing the crystals of a solvate to a particle size suitable for inhalation and thereafter contacting the micronised particles with chlorofluorocarbon propellents to form an aerosol formulation.

Canadian Patent Specification No. 1 147 652 discloses a method in which beclomethasone dipropionate is contacted with an alkane having from 5 to 8 carbon atoms to form a solvate and the crystalline material is reduced to a particle size suitable for inhalation and thereafter contacted with chlorofluorocarbon propellents to form an aerosol formulation.

British Patent Specification No. 2 052 506A discloses a process for making a hemihydrate crystalline form of flunisolide by crystallizing flunisolide from an aqueous solution of an alkanol. The patent also discloses that when solvents such as ethyl acetate and methanol are used for crystallization of flunisolide clathrate, solvate or related solvent inclusion complexes are formed.

Journal of Pharmaceutical Sciences, Vol. 52, No. 8, August 1963, pages 781-791 discloses the formation of a pentanol solvent of fluorocortisone acetate. All the dissolution investigations were conducted in aqueous media and there is no reference to aerosol formulations.

We have now found that chlorofluorocarbon propellent stable forms of beclomethasone dipropionate can be achieved by forming crystalline solvates with lower alkanols.

Therefore according to the present invention there is provided a method for preparing a stable aerosol formulation of a beclomethasone dipropionate in which the steroid is contacted with an alcohol containing 1 to 5 carbon atoms to form a crystalline solvate therewith, the crystalline material so formed being reduced to a particle size below 10 microns and thereafter dispersed in a composition comprising chloro-fluorocarbon propellents.

The process of the invention provides stable suspension aerosol formulations of beclomethasone dipropionate, in a simple and effective manner. The process has significant procedural advantages over the more complex methods disclosed in British Patent Specification No. 1 429 184, United Kingdom Patent Application No. GB 2076422 and Canadian Patent Specification No. 1 147 652. The formulation of the invention exhibits a better thermal stability than compositions employing solvates with ethyl acetate as disclosed in German Offenlegungsschrift No. 3 018 550.

The alcohols used in the invention are monohydric alkanols or alkenols having from 1 to 5 carbon atoms. The preferred alcohol for use in the invention is isopropyl alcohol.

The general procedure for solvate preparation is to dissolve the steroid in the minimum quantity of anhydrous alcohol with heating, e.g. 70° C. The resulting solution is cooled and allowed to stand for a sufficient time for solvate crystals to separate out. Preferably, the solution is cooled to 0° C. and maintained at this temperature for a period of about 24 hours. The solvate crystals may be filtered, dried and then micronised to the desired particle size, preferably in the range 2 to 5 microns.

The micronised particles may be incorporated into aerosol formulations by conventional techniques. The aerosol formulations containing the micronised solvates will generally simply comprise a suspension of the solvate in an appropriate propellent mixture together with a dispersing agent to stabilise the suspension. Suitable propellent mixtures generally comprise combinations or mixtures of Propellents 11, 12 and 114. Suitable dispersing agents include oleic acid, sorbitan trioleate and dioctyl sodium or calcium sulpho-succinate.

In order to precict long term particle size stability of solvates in aerosol formulations, short term crystal growth determinations in Propellent 11 have been made. It has been found that the tendency towards crystal growth exhibited by a suspension of the micronised solvate in Propellent 11 alone is markedly more pronounced than that which is observed with formulations containing other chlorofluorocarbon propellents. The reason for this effect is the significant polarity of Propellent 11 which is apt to promote drug dissolution (the first step towards recrystallisation and hence crystal growth); the most common constituent propellent of normal aerosol formulations is non-polar Propellent 12 and so dissolution occurs to a much lower degree.

It has been established that in the following Examples the level of crystal growth exhibited by a micronised solvate in Propellent 11 along after three hours storage at room temperature is approximately equivalent to that which is found after six months storage at room temperature of an equivalent aerosol formulation of the micronised solvate in Propellents 11, 12 and 114, and which contains not more than 10% of Propellent 11.

The invention will now be illustrated by the following Examples.

EXAMPLE 1

Preparation of a batch of aerosol units using the solvation technique (a) Preparation of beclomethasone dipropionate solvate with isopropyl alcohol Beclomethasone dipropionate (25 g) was dissolved under heat in isopropyl alcohol (200 ml). The solution was allowed to cool and then placed at 0° C. for 24 hours. The resulting crystalline solid was filtered under vacuum and vacuum dried to remove residual solvent. The product was then ground to a powder in a pestle and mortar and micronised in a Trost fluid energy mill.

(b) Preparation of suspension aerosol units 4.441 g of the solvate from a) was dispersed in 300 g Propellant 11 containing 2.221 g sorbitan trioleate.

This suspension was added to 854 g Propellant 114 and 4839 g Propellant 12 contained in a pilot scale aerosol cold-filling vessel at −60° C. The suspension was filled into 375 aluminium vials using a fill weight of 16 g per vial. The units were sealed with valves delivering 50 mcl of suspension. After six months storage no significant change had occurred in the suspension quality.

EXAMPLE 2

Beclomethasone dipropionate solvate preparation and particle size determination (a) Solvate Preparation Beclomethasone dipropionate (10 g) was dissolved under heat (approximately 70° C.) in the minimum quantity of alcohol. The solution was left at 0° C. for 24 hours by which time solvate crystals had separated out. The solvate crystals were Buchner filtered, vacuum dried to remove residual solvent and micronised using a Trost fluid energy mill.

(b) Suspension preparation

Solvate from the above process (200 mg) was suspended in Propellent 11 (50 g) containing oleic acid (0.1 mg/ml). The suspension was mixed for 5 minutes using a Silverson stirrer.

(c) Suspension particle size stability

Suspension particle size was assessed using a laser diffraction technique. The particle size of the micronised, solvated raw material was firstly determined in aqueous suspension. Samples of the suspensions, as prepared in (b), were then analysed after 3 hours storage at room temperature.

The following Table reports the alcohols used to prepare the solvates and the stability data.

| Particle size stability of micronised beclomethasone dipropionate and derived solvates by the laser diffraction technique. | | | | |
|---|---|---|---|---|
| Sample | | % < 2μ | % < 5μ | % < 10μ |
| commercial beclomethasone dipropionate | 1 | 56.9 | 100 | 100 |
| | 2 | 6.5 | 6.5 | 16 |
| ethanol solvate | 1 | 65.8 | 98.5 | 100 |
| | 2 | 29.3 | 45.7 | 79.5 |
| isopropyl alcohol solvate | 1 | 45.7 | 93.7 | 100 |
| | 2 | 42.3 | 88.2 | 100 |
| n-propanol | 1 | 53.1 | 86.5 | 100 |
| | 2 | 41.7 | 72.3 | 97.5 |
| n-butanol | 1 | 42.3 | 79.6 | 93.9 |
| | 2 | 20.6 | 36.7 | 66.3 |
| isobutanol | 1 | 38.6 | 72.9 | 95.6 |
| | 2 | 26.1 | 48.3 | 87.5 |
| n-pentanol | 1 | 62.4 | 100 | 100 |
| | 2 | 34.7 | 63.7 | 96.6 |

1 Particle size of micronised raw material
2 Particle size after suspension in Propellent 11 for 3 hours at room temperature.

Figure 1:
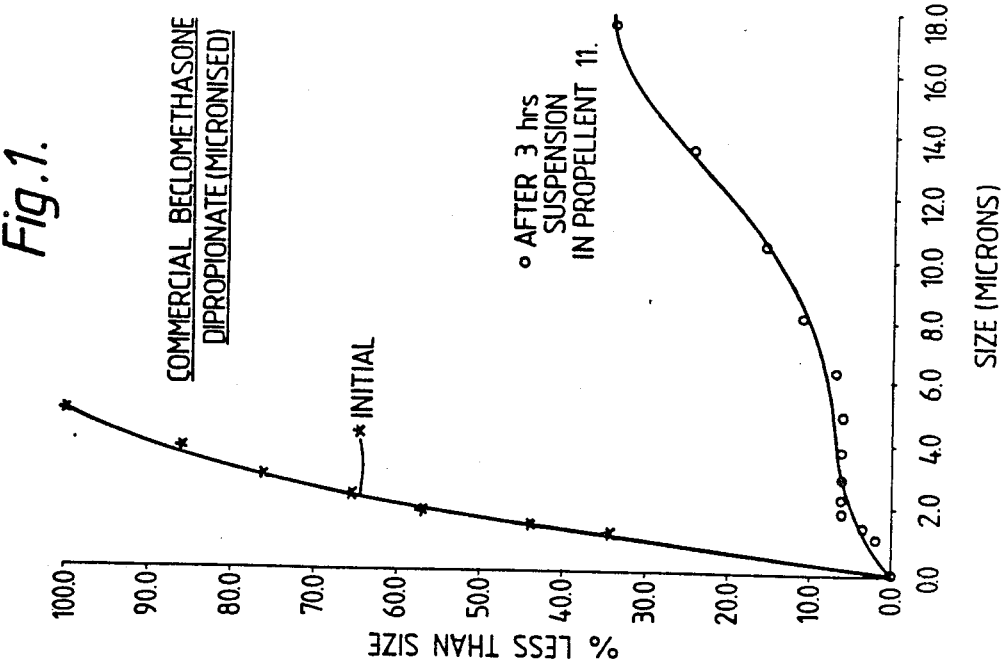

FIGS. 1 and 2 of the accompanying drawings represent profiles of the particle size stability of micronised commercial beclomethasone dipropionate and the micronised isopropyl alcohol solvate of beclomethasone dipropionate, respectively, after suspension in Propellent 11.

EXAMPLE 3

Solvation of beclomethasone dipropionate using methanol or allyl alcohol (2-propen-1-ol)

The methanol and allyl alcohol solvates of beclomethasone dipropionate were prepared and micronised according to the method in Example 1. The results of crystal growth experiments are reported in the following Table.

| Particle size stability of micronised beclomethasone dipropionate solvates by the laser diffraction technique. | | | | |
|---|---|---|---|---|
| Sample | | % < 2μ | % < 5μ | % < 10μ |
| methanol solvate | 1 | 71.1 | 97.0 | 100.0 |
| | 2 | 38.6 | 73.6 | 91.0 |
| allyl alcohol solvate | 1 | 37.4 | 68.0 | 96.1 |
| | 2 | 25.0 | 46.1 | 83.5 |

1 Particle size of micronised raw material.
2 Particle size after suspension in Propellent 11 for 3 hours at room temperature.

It will be seen that there was a marked increase in particle size stability over unsolvated material (see Example 2) although the level of crystal growth was higher with both solvates than that found with the isopropyl alcohol solvate.

EXAMPLE 4

Stability of a beclomethasone dipropionate isopropyl alcohol solvate aerosol formulation Batches of aerosols of the following formulation were prepared:

| | |
|---|---|
| Beclomethasone dipropionate isopropyl alcohol solvate (micronised) | 1.000 |
| Span 85 (sorbitan trioleate) | 0.500 |
| Propellant 11 | 67.550 |
| Propellant 114 | 192.293 |
| Propellant 12 | 1089.657 |
| | 1351.000 |

Particle size by the laser diffraction technique

| | % < 10.5μ | % < 5μ | % < 1.9μ |
|---|---|---|---|
| Time: Initial | | | |
| Unit 1 | 100 | 95.3 | 41.0 |
| Unit 2 | 100 | 95.9 | 45.9 |
| Time: 6 Months (room temperature storage) | | | |
| Unit 1 | 99.9 | 96.0 | 47.3 |
| Unit 2 | 100 | 92.6 | 41.8 |
| Time: 6 Months (cycling temperature; consecutive 12 | | | |

|  | % < 10.5μ | % < 5μ | % < 1.9μ |
|---|---|---|---|
| hour periods at 15 and 37° C.) | | | |
| Unit 1 | 100 | 83.9 | 34.6 |
| Unit 2 | 100 | 85.7 | 33.0 |

The results indicate that the particle size of the formulation is virtually unchanged after storage for six months at room temperature. After 6 months storage under cycling temperature conditions, some crystal growth was found although this was lower than than found in samples of two commercially available suspension aerosol formulations of beclomethasone dipropionate, namely "Becotide" and "Clenil" when subjected to identical conditions.

I claim:

1. A method for preparing a stable aerosol formulation of beclomethasone dipropionate in which beclomethasone dipropionate is contacted with an alcohol containing 1 to 5 carbon atoms to form a crystalline solvate therewith, the crystalline material so formed being reduced to a particle size below 10 microns and thereafter dispersed in a composition comprising chlorofluorocarbon propellents.

2. A method as claimed in claim 1, in which the alcohol is a monohydric alkanol or monohydric alkenol.

3. A method as claimed in claim 2, in which the alcohol is isopropyl alcohol.

4. A method as claimed in any preceding claim, in which beclomethasone dipropionate is dissolved in alcohol under heating, the resulting solution is cooled and allowed to stand for a sufficient time for solvate crystals to separate out and thereafter the solvate crystals are separated, dried to remove residual solvent and reduced to the desired particle size.

5. A method as claimed in claim 1, 2 or 3, in which the solvate crystals are reduced to a particle size in the range 2 to 5 microns.

6. An aerosol formulation comprising an aerosol propellent containing suspended therein, optionally in the presence of a dispersing agent, beclomethasone dipropionate in the form of a crystalline solvate with an alcohol containing 1 to 5 carbon atoms, the particle size of substantially all of the steroid material being such as to permit inhalation into the human bronchial system when dispensed as an aerosol.

7. A formulation as claimed in claim 6, in which the alcohol is monohydric alkanol or monohydric alkenol.

8. A formulation as claimed in claim 7, in which the alcohol is isopropyl alcohol.

9. A formulation as claimed in any one of claims 6 to 8, in which the solvate crystals are reduced to a particle size in the range 2 to 5 microns.

10. Beclomethasone dipropionate in the form of a crystalline solvate with an alcohol containing 1 to 5 carbon atoms, the particle size of substantially all of the steroid material being such as to permit inhalation into the human bronchial system when dispensed as an aerosol.

* * * * *